United States Patent [19]

Smith-Johannsen

[11] 4,369,151
[45] Jan. 18, 1983

[54] FREEZING ORGANIC PARTICULATE SLURRIES

[75] Inventor: Robert Smith-Johannsen, Incline Village, Nev.

[73] Assignee: Ramu International, Incline Village, Nev.

[21] Appl. No.: 215,399

[22] Filed: Dec. 11, 1980

[51] Int. Cl.$^3$ ............................................. B01J 13/00
[52] U.S. Cl. ................................. 264/28; 264/331.11; 252/317
[58] Field of Search ............................ 264/28, 331.11; 252/317

[56] References Cited

U.S. PATENT DOCUMENTS

| | | | |
|---|---|---|---|
| 3,171,870 | 3/1965 | Monteil | 264/28 |
| 3,177,161 | 4/1965 | Johannsen | 264/28 |
| 4,246,209 | 1/1981 | Johannsen | 264/28 |

*Primary Examiner*—John A. Parrish
*Attorney, Agent, or Firm*—Pennie & Edmonds

[57] ABSTRACT

Process of freezing organic particulate suspensions containing freeze-sensitive inorganic colloidal sols to form uniform porous substrates and of freezing biological material while in contact with a hydrophobic liquid.

12 Claims, No Drawings

FREEZING ORGANIC PARTICULATE SLURRIES

BACKGROUND OF THE INVENTION

Freezing a slurry of particulate ceramic material to form ceramic product has been disclosed in U.S. Pat. Nos. 3,177,161; 3,512,571; 3,816,572 and 3,885,005. The production of these ceramic structures in accordance with the prior art involves mixing an aqueous freeze-sensitive silical sol with the ceramic grains to form an aqueous slurry, freezing the slurry to form a frozen body, thawing and drying the body, and then firing the dried body.

SUMMARY OF THE INVENTION

This invention relates to a process of freezing organic particulate slurries or suspensions containing a freeze sensitive inorganic colloidal sol to a temperature where it spontaneously nucleates the slurry resulting in the formation of a very large number of ice crystals that are consequently very small thus producing an organic structure that is very uniform throughout. The invention further includes the addition of lithium ions to the freezing media with or without supercooling.

DETAILED DESCRIPTION AND PREFERRED EMBODIMENTS

Various organic particle dispersions can be frozen into porous structures and films in accordance with this invention including vinyl polymers, such as polyvinyl acetate, polyvinyl chloride, polyvinyl acetal, polyvinylidene chloride, and the like; acrylic polymers such as polyacrylic acid, polymethacrylic acid, polymethacrylate, polymethylmeacrylate, polyacrylonitrile, and the like. Further examples include polystyrene, polyethylene and derivatives of polyethylene, such as polyethylene terephthalate, synthetic rubbers such as polymerized chloroprene, and plasticized vinyl chloride. Copolymers and terpolymers can also be used, including butadiene-styrene copolymers, vinyl acetate-vinyl stearate copolymers, and the like. Biological or living tissue, such as cells, plant seeds, sperm, eggs and micro organisms, are also included herein as organic matter that can be frozen in accordance with this invention.

One of the objects of this invention is to freeze organic suspensions, latices or emulsions to form an organic porous structure or film and therefore the particle suspension to be frozen must be freeze sensitive; that is a dispersion which when frozen and thawed will not revert back to a suspension but will form an intergrated structure although the original organic suspension itself does not have to be freeze sensitive.

Many latices on the market today contain large amounts of hydrophilic stabilizers such as methyl cellulose designed to keep the particles apart from each other when frozen but will redisperse and reform the latex. Many of these dispersions, however, can be rendered freeze sensitive by incorporating therein a sufficient amount of freeze sensitive particles to render the entire dispersion or latex freeze sensitive. An example of such an addition as discussed herein is a freeze sensitive colloidal ceramic sol, such as sodium, lithium, or ammonia stabilized colloidal silica sol marketed by DuPont under the trade name "Ludox".

The suspensions containing the freeze sensitive colloidal ceramic sol should contain a sufficient amount or number of particles so that they touch each other when the suspension is frozen. Some organic resin dispersions may not contain a sufficient amount of organic particles to accomplish the above object, and it may be necessary to add additional particles to the suspensions. These additional particles may be organic resin particles or inorganic particles, such as clay, mica, etc.

The organic particle size is not critical but is advantageously as small and uniform as practical. The ultimate particle size will depend to some extent on the end use of the structures and the properties desired therein.

The organic products produced according to this invention are porous and the size of the grains or particles employed in the slurries will to a large extent determine the degree of porosity. The products of the invention have a wide variety of uses depending to some extent on the type of particle being employed in the process. For example, the products can be used in the same manner as other known porous or microporous resins are used, such as the so-called breathable films, filters, membranes, etc. Generally, the products are useful in any area where porosity is desired or in areas where porosity is not desired but is not detrimental. Biological matter is frozen for preservation or storage purposes.

The freeze-sensitive colloidal ceramic sols useful according to this invention are well known and include colloidal ceramic sols, such as disclosed in the Smith-Johannsen U.S. Pat. No. 3,177,161 and U.S. Pat. Nos. 3,512,571 to Phelps, 3,816,572 to Roelofs and 3,885,005 to Downing et al. A freeze-sensitive sol is one which, when frozen, will break down and no longer exist as a sol or colloidal suspension when thawed. Both cationic and anionic silica sols can be used with the anionic preferred. Ammonia stabilized silica sols, such as DuPont's AM LUDOX, may be advantageous where elimination of sodium is desired. Other freeze-sensitive colloidal ceramic sols, such as zirconia and magnesia sols, can also be used. Silica sols have been used because they are readily available on the market. Although not necessarily preferable due to insufficient experimental data to date, most present experiments mainly utilize a freeze-sensitive sodium stabilized colloidal silica sol having about 30% colloidal silica supplied by Nalco Chemical Company due to its availability.

The total amount of sol stabilizer such as sodium, ammonium and/or lithium, should be sufficient to stabilize the sol but not so high as to render the sol non-freeze sensitive. This can readily be determined by routine experimentation by one skilled in the art. For example, a mole ratio of silica to lithia of about 85 in a lithium stabilized silica sol works quite well but when the ratio is lowered to about 48 the sol appears to lose some freeze sensitivity resulting in weaker bonds. The optimum amounts have not as yet been determined.

When the lithium stabilized silica sol was used another new and very significant property was observed. These sols inhibited ice srystal growth even in the absence of supercooling. In fact, when nucleation was deliberately initiated, in the case of a dispersion containing lithium ions, from the surface with an ice crystal, no macro or large crystal growth was detectable for more than two millimeters from the initiation site. Thus the use of lithium stabilized ceramic sols has been found extremely advantageous for producing small uniform ice crystals during the freezing step. The use of a lithium stabilized ceramic sol in combination with supercooling has been found most advantageous.

When using lithium in the organic particle suspension containing a freeze sensitive cermic sol, it is of course most practicable to employ a lithium stabilized ceramic sol available on the market. A silica sol having a silica to lithia ratio of 85 worked quite well, however this sol, DuPont's Lithium Polysilicate 85, is not being marketed today. One lithium stabilized silica sol which is available today contains a silica to lithia ratio of about 48 (DuPont's Lithium Polysilicate 48. This amount of lithia however minimizes the freeze sensitivity of the sol and when used alone produced fired products having weaker bonds. This commercial lithium stabilized sol can be used however by using it in admixture with a sodium or preferably an ammonia stabilized sol. A 50-50 mixture has worked well but the optimum has not as yet been determined. It is the presence of the lithium ion which produces the surprising ice crystal growth inhibition rather than the absence of sodium or ammonia. Thus lithium ions can be added to the slurries by the addition of ionizable lithium compounds such as lithium chloride, lithium hydroxide, lithium sulfate, lithium succinate and so forth. It is preferred to add the lithium ions to the ceramic sol. The amount of lithium ions added to an organic particle slurry should be sufficient to inhibit ice crystal growth to the desired degree but insufficient to adversely affect the freeze sensitivity of the sol. This can be determined by routine experimentation with respect to any particular system being frozen. Only a very small amount of lithium ion is necessary to inhibit ice crystal growth.

To accomplish the supercooling and substantial instantaneous freezing, it is not a simple matter of inserting a mold filled with the suspension into a cold freezing media even at −40° or −60° F. This invention includes a process of insuring supercooling of the suspensions by wetting the mold with a hydrophobic or incompatible liquid such as xylene, mineral spirits, or percholorethylene to cover at least the entire working surface of the mold, and inserting the slurries or suspensions into the mold while it is still wet. This can be accomplished by simply dipping the mold in the hydrophobic liquid. The mold can then be closed and the slurry frozen. It is also advantageous to cover the aqueous slurry or suspension in the mold with a thin layer of the hydrophobic liquid. The mold itself is preferably of light weight and of low mass relative to the freezing media and the ceramic or particulate slurry being frozen. The mold and freezing media should also preferably have a high thermal conductivity. Although the freezing temperature can be varied, it should be sufficiently low to insure supercooling and a rapid freeze. Freezing temperatures can vary from 0° to −50° and lower. Precooling to near the freezing temperature before supercooling is also advantageous.

The supercooling can also be carried out without the use of a mold such as by extruding cylinders, sheets or films of the aqueous suspension on a belt treated with the hydrophobic liquid and then into the hydrophobic freezing media. The transport through the freezing media can be between the pair of belts and the process can be continuous. The terms "mold" as used herein is intended to include any structure for supporting and/or encompassing the slurries or suspensions.

Supercooling of the suspension to a temperature where it spontaneously nucleates results in a structure that is uniform throughout. At the time of nucleation not all the water freezes because the heat of fusion raises the temperature back to the freezing point. However, as cooling proceeds further, ice crystal growth is completed from all of these nucleation sites at substantially the same time. The structure that develops is therefore much more uniform and fine grained regardless of the thickness of the structure to be produced or frozen.

Random tests made on some of the freezing steps set forth herein indicate that the temperature of supercooling is about 4 degrees below the freezing temperatures of the aqueous slurry.

Various freezing media can be used to freeze the slurry structures such as those described in the above-mentioned patents. A hydrophobic freezing media such as freon or perchloroethylene is advantageously used to prevent penetration of the freezing media into the aqueous slurries to prevent the growth of large or variable sized ice crystals, and to insure supercooling.

The various organic particles useful according to this invention have different and known firing or sintering temperatures in conventional processes and these are described in the above U.S. Pat. No. 3,236,788.

The molds or patterns are usually made of lightweight steel or aluminum if more thermal conductivity is desired. The wetting of a mold with a hydrophobic liquid to aid in supercooling can also act as a release agent.

The suspensions should be as free from entrapped air as practical. Entrapped air can be avoided to some extent in the manner by which the slurries are first mixed, and any entrapped air can be removed in various known manners, such as using long periods of holding time, or vacuum treatment techniques.

After freezing, the frozen suspension structures are removed from the mold, thawed and dried. Although various manners of thawing and drying can be employed, the thawing and drying can be accelerated by the use of heat. The use of a conventional drying oven has been found satisfactory for this purpose.

The amount of the freeze-sensitive inorganic sol can be as reported in the above-noted U.S. patents. The most suitable percentage appears to be about 15% by weight of the colloidal ceramic sol (30% solids) based on the weight of the dried inorganic particles.

EXAMPLE

|  | Parts by wt. |
| --- | --- |
| Ammonia stabilized silica sol (30% solids) DuPont Ludox AS 40 | 12 |
| Lithium stabilized silical sol DuPont's Lithium Polysilicate 48 | 3 |
| Acrylic latex, Polymer Industrys Polycryl CR-48-A | 20 |
| Mica powder | 20 |

The above mixture was placed in a mold wetted with perchloroethylene, and then supercooled and frozen by immersion in perchloroethylene at about −40° C. The cast body was then thawed and dried. The body was porous and very uniform and retained its shape dimensions and shape.

This invention also includes the freezing biological matter or living tissue such as cells, plant seed, sperm, egg and microorganisms for preservation or storage purposes. An article in Science News Vol. 114 No. 12, pg. 202, September 1978, describes the current status in freezing techniques. It relates cell damage to inappropriate ice crystal growth. The important factor is considered to be the rate of cooling. Very rapid cooling causes smaller crystal growth inside and outside the cells which is disclosed as most desirable.

This invention involves the discovery that ice crystal morphology is only indirectly controlled by the cooling rate. it is really a function of nucleation and can only be controlled by controlling nucleation. In order to freeze biological matter, it must be contained in some sort of container and when frozen in a container, nucleation is a chance phenomenon. Chance premature nucleation from the container, no matter how clean it is, from the air, dust particles on the container wall, air borne ice crystals is great. Spontaneous nucleation can be accomplished with the substantial elimination of premature or chance nucleation, by supercooling the biological matter to be frozen, and then freezing at a low temperature on the order of −40 to −60 degrees C. Attempts to supercool before freezing are not consistantly successful when the biological matter is in contact with a solid surface due to nucleation by the container wall or dust particles. Supercooling can be obtained, however, by freezing the biological matter in contact with a hydrophobic water immiscible liquid or one which is incompatible with the biological matter to be frozen. This can be accomplished by coating the container walls with the hydrophobic liquid and inserting the biological matter into the container while it is still wet, supercooling the biological matter, and then freezing. The biological matter could also be immersed in a hydrophobic freezing liquid, supercooled and then frozen. Although the mold surface can be wetted with various hydrophobic liquids, it would be advantageous to use a non-toxic liquid such as one of the flourinated inert fluids such as perfluorohexane. Obviously where no structure is desired as is the case with biological matter there is no need for a freeze sensitive ceramic sol or sufficient particle concentration to form a structure.

I claim:

1. The process of freezing biological matter which comprises inserting the biological matter into a container having its walls wetted with a non-toxic hydrophobic liquid and while the walls of the container are still wet, freezing the biological matter.

2. The process according to claim 1 in which the biological matter is supercooled before the freezing thereof.

3. The process of freezing organic particle aqueous dispersions which comprises freezing the dispersions while in contact with a hydrophobic liquid.

4. The process according to claim 3 in which the organic dispersion is supercooled prior to freezing.

5. The process according to claims 3 or 4 in which the organic particle dispersion is frozen in the presence of lithium ions in a sufficient amount to eliminate large crystal growth.

6. The process for forming resinous porous structures which comprises mixing an aqueous suspension of resinous or plastic particles together with a freeze sensitive colloidal inorganic sol to form a freeze sensitive mixture having a sufficient amount of particles so that particles are in contact with each other and will form a bonded particle network when frozen, freezing the mixture to form a solid frozen mass and thawing the frozen mass to form a porous structure.

7. The process according to claim 6 in which the mixture is frozen while in contact with a hydrophobic liquid.

8. The process according to claims 6 or 7 in which the mixture contains inorganic particles in addition to the inorganic sol particles.

9. The process according to claims 6 or 7 in which the mixture is supercooled before freezing.

10. The process according to claims 6 or 7 in which the mixture contains lithium ions.

11. The process of freezing organic particle dispersions which comprises freezing the dispersion in the presence of lithium ions in a sufficient amount to inhibit large crystal growth.

12. The process of freezing biological matter which comprises supercooling the biological matter and then freezing the biological matter.

* * * * *